United States Patent
Hoelderich et al.

[11] Patent Number: 4,874,899
[45] Date of Patent: Oct. 17, 1989

[54] PREPARATION OF UNSATURATED AND SATURATED KETONES

[75] Inventors: Wolfgang Hoelderich, Frankenthal; Leopold Hupfer, Friedelsheim; Kurt Schneider, Bad Duerkheim, all of Fed. Rep. of Germany

[73] Assignee: BASF Aktiengesellschaft, Ludwigshafen, Fed. Rep. of Germany

[21] Appl. No.: 206,731

[22] Filed: Jun. 15, 1988

[30] Foreign Application Priority Data

Jun. 24, 1987 [DE] Fed. Rep. of Germany ....... 3720850

[51] Int. Cl.$^4$ ............................................. C07C 45/55
[52] U.S. Cl. ................................... 568/386; 568/309; 568/338
[58] Field of Search .................... 568/386, 338, 309

[56] References Cited

FOREIGN PATENT DOCUMENTS

| | | | |
|---|---|---|---|
| 1109669 | 1/1962 | Fed. Rep. of Germany ...... | 568/386 |
| 2758113 | 5/1979 | Fed. Rep. of Germany ...... | 568/319 |
| 0658801 | 5/1965 | France .............................. | 568/319 |
| 0993389 | 5/1965 | United Kingdom .............. | 568/390 |

OTHER PUBLICATIONS

Cardillo et al., Chem. Abst., vol. 100, #85234k, (1984).

*Primary Examiner*—James H. Reamer
*Attorney, Agent, or Firm*—Keil & Weinkauf

[57] ABSTRACT

Unsaturated ketones of the formula

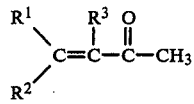

and saturated ketones of the formula

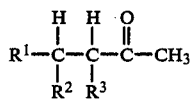

where $R^1$, $R^2$ and $R^3$ are each hydrogen, alkyl of 1 to 12 carbon atoms or a cycloalkyl, aryl, aralkyl or alkylaryl radical which in turn may be substituted, or $R^1$ and $R^3$ or $R^2$ and $R^3$, together with the carbon atoms to which they are bonded, may form a cycloalkane, are prepared by a process in which a 5-methylene-1,3-dioxolanone which is substituted in the 4-position and is of the forumla

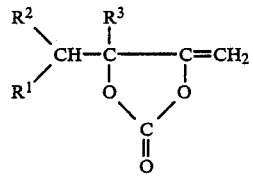

where $R^1$, $R^2$ and $R^3$ have the above meanings, (a) for the preparation of an unsaturated ketone, is converted in the presence of a zeolite, of a phosphate having a zeolite structure and/or of B, Ce, Fe, Zr or Sr phosphate as catalysts and (b) for the preparation of a saturated ketone, is converted in the presence of the same catalysts which additionally carry one or more hydrogenation components.

5 Claims, No Drawings

PREPARATION OF UNSATURATED AND SATURATED KETONES

The present invention relates to a process for the preparation of unsaturated and saturated ketones by decarboxylation of 5-methylene-1,3-dioxolanones which are substituted in the 4-position.

Because of their wide range of possible uses, ketones are desirable chemical compounds. Saturated ketones are used, for example, as solvents in the rubber and plastics industry, as solvents in chemical reactions, as extracting agents or as starting materials for organic reactions, for example as intermediates for dyes, crop protection agents and pharmaceutical products, and as fragrance materials.

Bifunctional compounds are useful building blocks for organic syntheses. This class of compounds also includes the $\alpha,\beta$-unsaturated ketones. These ketones are used, inter alia, for the synthesis of compounds having physiological activity. Another field of use for the $\alpha,\beta$-unsaturated ketones, in particular methyl isopropenyl ketone, is in the chemistry of heat-stable polymers and copolymers. Methyl isopropenyl ketone is used as a monomer for poly-(isopropenyl methyl ketone) or as a copolymer with polybutadiene or PVC. Such ketones are also employed in the preparation of epoxy resins.

It is known that $\alpha,\beta$-unsaturated ketones can be prepared by aldol condensation of aliphatic ketones and formaldehyde in the presence of oxalic acid or in the presence of cation exchangers and $H_2O$ under superatmospheric pressure (British Pat. No. 993,389 or French Pat. No. 1,383,548) or by reaction of enol acetates with ketones in the presence of Lewis acids, such as $BF_3$ or $TiCl_4$, or by oxidation of branched olefins in 50% strength acetic acid and in the presence of $PdCl_2$ as a catalyst (Belgian Pat. No. 658,801) or by condensation of saturated carbonyl compounds in the presence of $BF_3$.

There is furthermore a multistage process in which $\alpha,\beta$-unsaturated ketones are obtained by condensation of ketones in the presence of tosylmethyl isocyanide, followed by alkylation and hydrolysis. Other expensive preparation processes are, for example, the ozonolysis of 2,3-dimethylbutadienes or the anodic oxidation of $\beta$-ketocarboxylates or the photoisomerization of 1,2-diacylcyclobutanes. The gas-phase oxidation of olefins with metal oxide/phosphorous oxide catalysts leads to a mixture of various compounds, including $\alpha,\beta$-unsaturated ketones.

For the preparation of the saturated ketones, the unsaturated ketones can be hydrogenated by a conventional method.

The known processes for the preparation of unsaturated, and therefore also of saturated, ketones have various disadvantages, ie. they start from starting compounds which are difficult to obtain or use toxic and corrosive homogeneous catalysts, or an energy-consumptive or multistage reaction procedure, such as ozonolysis or photoisomerization, has to be accepted. Particularly in the industrial production of asymmetrically substituted ketones, it is necessary as a rule to rely on the condensation of different organic acids with decarboxylation, as described in German Laid-Open Application DOS 2,758,113 and in Houben-Weyl, 1973, Vol. 7/2a, Ketone I, page 627 et seq. In this process, the inevitable production of symmetrically substituted ketones and carbon dioxide is a disadvantage.

A great disadvantage of the preparation of saturated ketones from precursors of the unsaturated ketones is the two-stage procedure.

Furthermore, German Pat. No. 1,109,669 discloses that dioxolanones can be decarboxylated to give unsaturated ketones. This process is preferable carried out by heating in the liquid phase. In order to ensure a smooth reaction, the presence of high boiling solvents is necessary. These have to be removed again after the reaction by an expensive distillation procedure.

It is an object of the present invention to synthesize unsaturated and saturated ketones, in particular asymmetrically substituted ketones, by a simple reaction from readily available starting compounds in short residence times with high selectivity and space-time yields.

We have found that this object is achieved and that the disadvantages described above are avoided and unsaturated ketones of the formula (I)

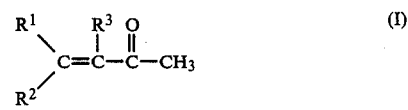

and saturated ketones of the formula (II)

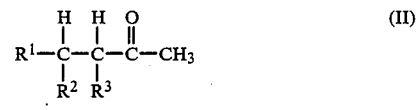

where $R^1$, $R^2$ and $R^3$ are each hydrogen, alkyl of 1 to 12 carbon atoms or a cycloalkyl, aryl, aralkyl or alkylaryl radical which in turn may be substituted, or $R^1$ and $R^3$ or $R^2$ and $R^3$, together with the carbon atoms to which they are bonded, may form a cycloalkane, are obtained in a simple manner, if a 5-methylene-1,3-dioxolanone which is substituted in the 4-position and is of the formula (III)

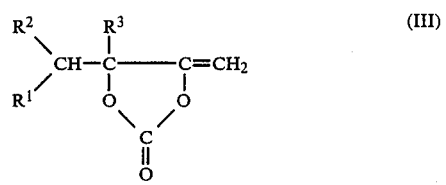

where $R^1$, $R^2$ and $R^3$ have the above meanings, (a) for the preparation of unsaturated ketones (I), is converted in the presence of a zeolite, of a phosphate having a zeolite structure and/or a B, Ce, Fe, Zr or Sr phosphate as catalysts and (b) for the preparation of saturated ketones (II), is converted in the presence of hydrogen over a zeolite, a phosphate having a zeolite structure and/or a B, Ce, Fe, Zr or Sr phosphate, which carries one or more hydrogenation components, as catalysts. Examples of suitable starting materials are the following 5-methylene-4,4-dialkyl-1,3-dioxolanones: 5-methylene-4,4-dimethyl-1,3-dioxolan-2-one, 5-methylene-4,4-diethyl-1,3-dioxolan-2-one, 5-methylene-4-methyl-4-ethyl-1,3-dioxolan-2-one, 5-methylene-4-methyl-4-(4'-methylpent-3'-enedioxolan-2-one, 5-methylene-4-methyl-4-butyl-1,3-dioxolan-2-one and 5-methylene-4-methyl-4-n-octyl-1,3-dioxolan-2-one. Starting compounds in which $R^1$ and $R^3$ or $R^2$ and $R^3$ together form an alkyl radical, for example the propylidene, tetramethylene or hexmethylene radicals, are, for example, 5-methylene-4,4-spirohexamethylene-1,3-dioxolan-2-one and 5-methylene-4,4-spiropentamethylene-1,3-dioxolan-2-one.

The substituted methylenedioxolanones are obtainable, for example, by reacting an acetylene alcohol with carbon dioxide in the presence of a catalyst, eg. a copper salt.

For the purposes of the present invention, suitable catalysts are in general zeolites of the pentasil type, such as aluminosilicate zeolites, borosilicate zeolites, iron silicate zeolites and zeolites of the faujasite type, which may furthermore carry a hydrogenation component.

The zeolites may be doped with, for example, alkali metals, transition metals and rare earth metals, if necessary in addition to the hydrogenation components.

However, phosphates of the elements B, Ce, Zr, Fe or Sr or a mixture of these may also be used as catalysts. For example, phosphates prepared by a hydrothermal process are also suitable catalysts, eg. hydrothermally prepared aluminum phosphates, silicon aluminum phosphates, iron aluminum phosphates and boron aluminum phosphates. For the preparation of the saturated ketones, these catalysts furthermore carry one or more hydrogenation components.

The zeolites are advantageously used in the acidic form as catalysts for the novel process.

In the zeolites, instead of aluminum, it is also possible for other elements, such as B, Ga, Fe, Cr, V, As, Sb, Bi or Be or a mixture of these to be incorporated in the framework, or for the silicon to be received by a tetravalent element, such as Ge, T, Zr or Hf.

Zeolites are subdivided into various groups, depending on their structure. For example, the zeolite structure is formed by chains in the mordenite group or by sheets of tetrahedra in the chabasite group, whereas in the faujasite group the tetrahedra are arranged to form polyhedra, for example in the form of a cubooctahedron which consists of four-membered rings and six-membered rings. Depending on the bonding of the cubooctahedra, giving cavities and pores of different sizes, a distinction is made between zeolites of type A, L, X and Y.

Other suitable catalysts for the novel process are zeolites from the mordenite group or fine-pore zeolites of the erionite or chabasite type or zeolites of the faujasite type, eg. Y, X or L zeolites.

This group of zeolites also includes the ultra-stable zeolites of the faujasite type, ie. zeolites from which aluminum has been removed.

Zeolites of the pentasil type are particularly advantageous. They have a five-membered ring consisting of $SiO_4$ tetrahedra as a common building block and possess a high $SiO_2/Al_2O_3$ ratio as well as pore sizes which are between those of the zeolites of type A and those of type X or Y.

These zeolites can have different chemical compositions. They are aluminosilicate, borosilicate, iron silicate, beryllium silicate, gallium silicate, chromium silicate, arsenosilicate, antimony silicate and bismuth silicate zeolites or mixtures of these, and aluminogermanate, borogermanate, gallium germanate and iron germanate zeolites or mixtures of these. The aluminosilicate, borosilicate and iron silicate zeolites of the pentasil type are particularly suitable for the novel process. The aluminosilicate zeolite is prepared, for example, from an aluminum compound, preferably $Al(OH)_3$ or $Al_2(SO_4)_3$, and a silicon component, preferably finely divided silica, in aqueous amine solution, in particular in a polyamine, such as 1,6-hexanediamine or 1,3-propanediamine or triethylenetetramine solution, with or, in particular, without the addition of an alkali metal compound or alkaline earth metal compound, at from 100° to 220° C. under autogenous pressure. These also include the isotactic zeolites according to European Pat. Nos. 34,727 and 46,504. The aluminosilicate zeolites obtained have an $SiO_2/Al_2O_3$ ratio of from 10 to 40,000, depending on the amounts of starting materials chosen. Aluminosilicate zeolites of the pentasil type can also be synthesized in an ether medium, such as diethylene glycol dimethyl ether, in an alcoholic medium, such as methanol or butane-1,4-diol or in water.

The silicon-rich zeolites ($SiO_2/Al_2O_3 \geq 10$) which can be used according to the invention also include the various ZSM types, ferrierite, Nu-1 and Silicalit ®.

Borosilicate zeolites can be synthesized, for example, at from 90° to 200° C. under autogenous pressure by reacting a boron compound, eg. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali metal compound or alkaline earth metal compound. These include the isotactic zeolites according to European Pat. Nos. 34,727 and 46,504. Such borosilicate zeolites can also be prepared if the reaction is carried out in ether solution, eg. diethylene glycol dimethyl ether, or in alcoholic solution, eg. hexane-1,5-diol, instead of in aqueous amine solution.

The iron silicate zeolite is obtained, for example from an iron compound, preferably $Fe_2(SO_4)_3$, and a silica compound, preferably finely divided silica, in aqueous amine solution, in particular, 1,6-hexanediamine, with or without the addition of an alkali metal compound or alkaline earth metal compound, at from 100° to 200° C. under autogenous pressure.

The aluminosilicate, borosilicate and iron silicate zeolites thus prepared can be isolated, dried at from 100° to 160° C. and calcined at from 450° to 550° C., preferably 500° C., and then molded with a binder in a weight ratio of from 90:10 to 40:60 to give extrudates of pellets. Suitable binders are various aluminas, preferably boehmite, amorphous aluminosilicates having an $SiO_2/Al_2O_3$ ratio of from 25:75 to 90:5, preferably 75:25, silica, preferably finely divided $SiO_2$, mixtures of finely divided $SiO_2$ and finely divided $Al_2O_3$, $TiO_2$, $ZrO_2$ and clay. After the molding procedure, the extrudates or pellets are dried at 110° C. for 16 hours and calcined at 500° C. for 16 hours.

Advantageous catalysts are also obtained if, for eample, the aluminosilicate or borosilicaate zeolite isolated is molded directly after drying and not subjected to calcination until after the molding procedure. The aluminosilicate and borosilicate zeolites prepared can be used in pure form, without a binder, as extrudates or pellets, the extrusion or peptizing assistance used being, for example, ethylcellulose, stearic acid, potato starch, formic acid, oxalic acid, acetic acid, nitric acid, ammonia, amines, silicoesters and graphite or mixtures of these.

If, because of its method of preparation, the zeolite is not in the catalytically active, acidic H form but, for example, in the Na form, this form can be completely or partially converted into the desired H form by ion exchange, for example with ammonium ions, followed by calcination, or by treatment with an acid.

This doping is advantageously carried out as follows: the molded zeolite is initially taken in a riser tube and an aqueous or ammoniacal solution of a halide or of a nitrate of the metals described above is passed over the said zeolite at from 20° to 100° C. Ion exchange of this type can be carried out on the hydrogen, ammonium and alkali metal form of the zeolites. In another possible method for applying the metals to the zeolite, the zeolite material is impregnated, for example with a halide, a nitrate or an oxide of the metals described above in aqueous alcoholic or ammoniacal solution. Both ion exchange and impregnation are followed by one or more drying steps and, if desired, repeated calcination.

In a possible embodiment, $Cu(NO_3)_2.3H_2O$ or $Ni(NO_3)_2.6H_2O$ or $Ce(NO_3)_3.6H_2O$ or $La(NO_3)_2.6H_2O$ or $Pd(NO_3)_2$ is dissolved in water and this solution is used to impregnate the molded or unmolded zeolite for a certain time, eg. 30 minutes. Any supernatant solution is freed from water in a rotary evaporator. Thereafter, the impregnated zeolite is dried at about 150° C. and calcined at about 550° C. This impregnating process can be carried out several times in succession in order to obtain the desired metal content.

It is also possible to prepare an aqueous $Ni(NO_3)_2$ solution or ammoniacal $Pd(NO_3)_2$ solution and to suspend the pure zeolite powder therein at from 40° to 100° C. for about 24 hours while stirring. After the product has been filtered off, dried at about 150° C. and calcined at about 500° C., the zeolite material thus obtained can be further processed with or without a binder to give extrudates, pellets or fluidizable material.

Ion exchange with the zeolite present in the H form or ammonium form or alkali metal form can be carried out by initially taking the zeolite, in the form of extrudates or pellets, in a column, and circulating an aqueous $Co(NO_3)_2$, $Ni(NO_3)_2$ or $Fe(NO_3)_2$ solution or ammoniacal $Pd(NO_3)_2$ solution over the said zeolite at slightly elevated temperatures of from 30° to 80° C. for from 15 to 20 hours. The product is then washed thoroughly with water, dried at about 150° C. and calcined at about 550° C. In the case of some metal-doped zeolites, for example Pt-, Pd-, Cu-, Co- or Ni-doped zeolites, an aftertreatment with hydrogen is advantageous.

In many cases, it is also advantageous to reduce the catalyst before the beginning of the reaction. For example, a Pt—, Pd—, Co—, Ni—, Fe—, Rh—, Ru— or Co-doped zeolite catalyst is heated in a reactor to 170°–220° C. under $N_2$, after which $H_2$ is slowly introduced. The temperature is kept constant until $H_2O$ no longer emerges. A reduction method is also described in J. of Catal. 89 (1984), 520–526.

By impregnating and ion exchange, it is also possible simultaneously to apply a plurality of metals as hydrogenation components.

To achieve very high selectivity, high conversions and long catalyst lives, it may be advantageous to modify the zeolites. In a suitable method of modifying the catalysts, for example, the unmolded or molded zeolite is doped with metal salts by ion exchange or by impregnation, in addition to the abovementioned hydrogenation components. The metals used are alkali metals, such as Li, Cs or K, alkaline earth metals, such as Mg, Ca, Sr or Ba, metals of main groups 3, 4 and 5, such as B, Al, Ga, Ge, Sn, Pb or Bi, or rare earth metals, such as La, Ce, Pr, Nd, Er, Yb or U. Modification with these metals can be carried out simultaneously with application of the hydrogenation component by ion exchange or impregnation or before application of the hydrogenation components or after application of the hydrogenation component and any subsequent calcination.

In another possible method of modification, the molded or unmolded zeolite material is subjected to a treatment with acids, such as hydrochloric acid, hydrofluoric acid and phosphoric acid and/or steam. After this type of modification, the hydrogenation components are applied. Specifically, in an advantageous procedure, zeolites in powder form are treated with 1N phosphoric acid for 1 hour at 80° C. After the treatment, the product is washed with water, dried at 100° C. for 16 hours and calcined at 500° C. for 20 hours. In another procedure, zeolites, before or after they have been molded with a binder, are treated with a 3–25, in particular 12–20, % strength by weight aqueous hydrochloride acid, for example for from 1 to 3 hours at from 60° to 80° C. The zeolite treated in this manner is then washed with water, dried, and calcined at from 400° to 500° C. The hydrogenation component is then applied by ion exchange or impregnation, as described above.

In another particular embodiment of the acid treatment, the zeolite material, before being molded, is treated at elevated temperatures with from 0.001 to 2N, preferably from 0.05 to 0.5N, hydrofluoric acid, for example by refluxing for from 0.5 to 5, preferably from 1 to 3, hours. After the zeolite material has been isolated, for example by filtering it off and washing it thoroughly, it is advantageously dried at from 100° to 140° C. and calcined at from 450° to 600° C. In another preferred embodiment of the acid treatment, the zeolite material is molded with a binder and then advantageously treated with, preferably, from 12 to 20% strength by weight hydrochloric acid at from 50° to 90° C., in particular from 60° to 80° C., for from 0.5 to 5 hours. Advantageously, the zeolite material is then washed thoroughly, dried at from 100° to 160° C. and calcined at from 450° to 600° C. An HF treatment can be followed by an HCl treatment. The hydrogenation component is then applied as described above.

In another procedure, zeolites can be modified by applying phosphorus compounds, such as trimethyl phosphate, trimethoxyphosphine or primary, secondary or tertiary sodium phosphate. Treatment with primary sodium phosphate has proven particularly advantageous. In this procedure, the zeolites, in the form of extrudates, pellets or fluidizable material, are impregnated with aqueous $NaH_2PO_4$ solution, dried at 110° C. and calcined at 500° C. Thereafter, the hydrogenation component is applied.

If deactivation due to coking takes place when the zeolite catalysts and the other catalysts used for this purpose are employed according to the invention, it is advisable to regenerate these catalysts by burning off the coke deposits with air or with an $air/N_2$ mixture at from 400° to 550° C., preferably 500° C. The zeolites then regain their initial activity.

By precoking, it is possible to adjust the activity of the catalyst to obtain optimum selectivity with regard to the desired reaction product.

Other catalysts for the preparation of saturated and unsaturated ketones are phosphates having a zeolite structure, such as aluminum phosphates, silicon aluminum phosphates, silicon iron aluminum phosphates, iron aluminum phosphates, boron aluminum phosphates and mixtures of these.

Synthetic aluminum phosphates are used as aluminum phosphate catalysts for the novel process, particularly under hydrothermal conditions. Examples of suitable aluminum phosphates are APO-5, APO-9, APO-11, APO-12, APO-14, APO-21, APO-25, APO-31 and APO-33.

For example, ALPO$_4$-5 (APO-5) is synthesized by homogeneously mixing orthophosphoric acid with pseudoboehmite (Catapal SB R) in water, adding tetrapropylammonium hydroxide to this mixture and then carrying out the reaction at about 150° C. for from 20 to 60 hours under autogenous pressure in an autoclave. The AlPO$_4$ filtered off is dried at from 100° to 160° C. and calcined at from 450° to 550° C.

AlPO$_4$-9 (APO-9) is likewise synthesized from orthophosphoric acid and pseudoboehmite, but in aqueous DABCO (1,4-diazabicyclo[2.2.2]octane) solution at about 200° C. under autogenous pressure in the course of from 200 to 400 hours. If ethylenediamine is used instead of DABCO solution, APO-12 is obtained.

AlPO$_4$-21 (APO-21) is synthesized from orthophosphoric acid and pseudoboehmite in aqueous pyrrolidine solution at from 150° to 200° C. under autogenous pressure in the course of from 50 to 200 hours.

Known silicon aluminum phosphates, such as SAPO-5, SAPO-11, SAPO-31 and SAPO-34, can also be used for the novel process. These compounds are prepared by crystallization from an aqueous mixture at from 100° to 250° C. under autogenous pressure in the course of from 2 hours to 2 weeks, the reaction mixture which is reacted comprising a silicon component, an aluminum component and a phosphorus component in aqueous solutions containing organic amines.

SAPO-5 is obtained, for example, by mixing SiO$_2$, suspended in aqueous tetrapropylammonium hydroxide solution, with an aqueous suspension of pseudoboehmite and orthophosphporic acid and then carrying out the reaction at from 150° to 200° C. in the course of from 20 to 200 hours under autogenous pressure in a stirred autoclave. The powder filtered off is dried at from 110° to 160° C. and calcined at from 450° to 550° C.

Other suitable silicon aluminum phosphates are ZYT-5, ZYT-6, ZYT-7, ZYT-9, ZYT-11 and ZYT-12.

Other phosphate catalysts which may be used in the process are precipitated phosphates of the elements B, Zr, Fe, Ce and Sr.

Boron phosphates as catalysts for the novel process can be prepared, for example, by mixing and kneading concentrated boric acid and phosphoric acid and then drying and calcining the product in an inert gas, air or steam atmosphere at from 250° to 650° C., preferably from 300° to 500° C.

Cerium phosphates as catalysts can be obtained, for example, by precipitation from an aqueous cerium salt solution with an alkali metal phosphate.

The hydrogenation components are applied as described above on these phosphates, either phosphates having a zeolite structure or precipitated phosphates, by impregnation (dipping or spraying on) or in some cases by ion exchange. As in the case of the zeolite catalysts, modification with metals or acids is also possible. In this case too, the hydrogenation component is applied thereafter. Any modification with metals or acids may be carried out beforehand or afterward.

The catalysts described here can be used alternatively in the form of 2-4 mm extrudates, pellets of 3-5 mm diameter or chips having particle sizes of from 0.1 to 0.5 mm or as fluidized catalysts.

The reaction conditions generally selected for the novel conversion are, in the preferred gas phase, from 100° to 500° C., eg. from 150° to 450° C., in particular from 300° to 400° C., and a WHSV of from 0.1 to 20 h$^{-1}$ (g of starting material per g of catalyst per hour). The reaction is preferably carried out in a fixed bed or fluidized bed.

It is also possible to carry out the reaction in the liquid phase by the suspension, trickle-bed or liquid phase method, at from 50° to 200° C.

The molar ratio of hydrogen to dioxolanone can be from 1 to 100, in particular from 3 to 30, for the preparation of the saturated ketones.

The process is generally carried out under atmospheric pressure or, depending on the volatility of the starting compound, under reduced or superatmospheric pressure, batchwise or, preferably, continuously.

Sparingly volatile or solid starting materials can be used in dissolved form, for example in solution in tetrahydrofuran, toluene or petroleum ether. The starting material may furthermore be diluted with such solvents or with inert gases, such as N$_2$, Ar or steam.

After the reaction, the resulting products are further processed directly or are isolated from the reaction mixture by a conventional method, for example by distillation. Unconverted starting materials are, if desired, recycled to the reaction.

EXAMPLES 1 TO 20

The reaction is carried out in the gas phase under isothermal conditions in a tube reactor (coil, 0.6 cm internal diameter, 90 cm length) for not less than 6 hours. The reaction products are isolated and characterized by conventional methods. Quantitative determination of the reaction products and of the starting materials is carried out by gas chromatography.

The following catalysts are used for the Examples.

Catalyst A

A borosilicate zeolite of the pentasil type is prepared in a hydrothermal synthesis from 640 g of finely divided SiO$_2$, 122 g of H$_3$BO$_3$ and 8,000 g of an aqueous 1,6-hexanediamine solution (weight ratio 50:50) at 170° C. under autogenous pressure in a stirred autoclave. The crystalline reaction product is filtered off, washed thoroughly, dried at 100° C. for 24 hours and then calcined at 500° C. for 24 hours. This borosilicate zeolite is composed of 94.2% by weight of SiO$_2$ and 2.3% by weight of B$_2$O$_3$. It is molded with a molding assistant to give 2 mm extrudates, which are dried at 110° C. for 16 hours and calcined at 500° C. for 24 hours.

Catalyst B

An aluminosilicate zeolite of the pentasil type is prepared under hydrothermal conditions, under autogenous pressure and at 150° C., from 65 g of finely divided SiO$_2$, 20.3 g of Al$_2$(SO$_4$)$_3$.18H$_2$O in 1 kg of an aqueous 1,6-hexanediamine solution (weight ratio 50:50) in a stirred autoclave. The crystalline reaction product is filtered off, washed thoroughly, dried at 110° C. for 24 hours and then calcined at 500° C. for 24 hours. The aluminosilicate zeolite contains 96.1% by weight of SiO$_2$ and 4.6% by weight of Al$_2$O$_3$. The catalyst is converted into 2 mm extrudates, which are dried at 110° C. for 16 hours and calcined at 500° C. for 24 hours.

Catalyst C

An iron silicate zeolite of the pentasil type is synthesized under hydrothermal conditions, under autogenous pressure and at 165° C., from 273 g of waterglass, dissolved in 253 g of an aqueous 1,6-hexanediamine solution (weight ratio 50:50) and 31 g of iron sulfate, dissolved in 21 g of 96% strength sulfuric acid and 425 g of water, in a stirred autoclave in the course of 4 days. The zeolite is filtered off, washed thoroughly, dried at 110° C. for 24 hours and calcined at 500° C. for 24 hours. The resulting iron silicate zeolite has an $SiO_2/Fe_2O_3$ ratio of 17.7 and an $Na_2O$ content of 1.2% by weight. The zeolite is extruded with finely divided $SiO_2$ in a weight ratio of 80:20 to give 2.5 mm extrudates, which are dried at 110° C. for 16 hours and calcined at 500° C. for 24 hours. The product is then subjected to ion exchange with a 20% strength $NH_4Cl$ solution at 80° C. until the Na content is 0.002% by weight after drying at 110° C. and calcination at 500° C. for 5 hours.

Catalyst D

Catalyst D is obtained by impregnating catalyst A with $Ce(NO_3)_3$ solution and then drying the product at 130° C. for 2 hours and calcining it at 540° C. for 2 hours. The Ce content is 1.7% by weight.

Catalyst E $AlPO_4$-5 (APO-5) is synthesized by dissolving 200 g of 96% strength phosphoric acid, and suspending 136 g of boehmite, in 335 g of water, adding 678 g of a 30% strength aqueous tetrapropylammonium hydroxide solution and reacting this mixture in a stirred autoclave at 150° C. for 43 hours under autogenous pressure. The crystalline material is filtered off, dried at 120° C. and then calcined at 500° C. for 16 hours. The $AlPO_4$-5 synthesized in this manner contains 46.5% by weight of $P_2O_5$ and 45.5% by weight of $Al_2O_3$. This material is molded with boehmite in a weight ratio of 60:40 to give 2 mm extrudates, which are repeatedly dried at 120° C. and calcined at 500° C. for 8 hours.

Catalyst E $AlPO_4$-12 (APO-12) is synthesized by dissolving 200 g of 98% strength phosphoric acid, and suspending 136 g of boehmite, in 721 g of water, adding 30 g of ethylenediamine and reacting this mixture in a stirred autoclave at 200° C. for 24 hours under autogenous pressure. The crystalline material is filtered off, dried at 120° C. and calcined at 500° C. for 16 hours. The $AlPO_4$-12 synthesized in this manner contains 56.1% by weight of $P_{25}$ and 43.1% by weight of $Al_2O_3$. The material is molded with boehmite in a weight ratio of 60:40 to give 2 mm extrudates, which are repeatedly dried at 120° C. and calcined at 500° C. for 8 hours.

Catalyst G

SAPO-5 is prepared from a mixture of 200 g of 98% strength phosphoric acid, 136 g of boehmite, 60 g of 30% strength silica sol, 287 g of tripropylamine and 587 g of $H_2O$. This mixture is reacted at 150° C. for 168 hours under autogenous pressure. The crystalline product is filtered off, dried at 120° C. and calcined at 500° C. SAPO-5 contains 49.8% by weight of $P_2O_5$, 33.0% by weight of $Al_2O_3$ and 6.2% by weight of $SiO_2$. SAPO-5 is molded with a molding assistant to give 3 mm extrudates, which are dried at 120° C. and calcined at 500° C.

Catalyst H $CePO_4$ is obtained by precipitation from 52 g of $Ce(NO_3)_3.6H_2O$ and 56 g of $NaH_2PO_4.2H_2O$. The material is filtered off and then converted to extrudates, and then dried at 120° C. and calcined at 450° C. Catalyst H contains 47.1% by weight of Ce and 12.7% by weight of P.

Catalyst I

Commercial zirconium phosphate is molded with a molding assistant to give 2 mm extrudates, which are dried at 110° C. and calcined at 500° C. for 16 hours.

Catalyst J $BPO_4$ is prepared by combining 49 g of $H_3BO_3$ with 117 g of 75% strength $H_3PO_4$ in a kneader, evaporating off excess water and molding the reaction product to give 3 mm extrudates. The extrudates are dried at 100° C. and calcined at 350° C. Catalyst J contains 8.77% by weight of B and 28.3% by weight of P.

The results obtained with catalysts A to J described above and the reaction conditions are shown in Table 1 below. The samples were analyzed after a reaction time of 6 hours. After prolonged standing, the dimer of isopropenyl methyl ketone formed. This can be suppressed by adding, for example, hydroquinone and by cooling.

Catalyst K

Catalyst K is obtained by impregnating the extrudates of catalyst A with an aqueous $Cu(NO_3)_2$ solution and then carrying out drying at 130° C. for 2 hours and calcination at 540° C. for 2 hours. The Cu content is 3.4% by weight.

Catalyst L

The extrudates of the borosilicate zeolite, as described for catalyst A, are initially taken in a column and are subjected to ion exchange with an ammoniacal palladium nitrate solution at 50° C. The product is washed thoroughly with $H_2O$, dried at 110° C. and calcined at 500° C. for 5 hours. The Pd content is 1.9% by weight.

Catalyst M

Catalyst M is prepared similarly to catalyst K, but is impregnated with an aqueous solution of Pd nitrate and Pr nitrate, instead of Cu nitrate. The Pd content is 1.0% by weight and the Pr content is 4.6% by weight.

Catalyst N

Catalyst N is obtained by subjecting catalyst G to ion exchange with palladium nitrate, as described for catalyst L. The Pd content is 1% by weight.

The experimental results obtained with catalysts K-N in the presence of hydrogen are summarized in Table 2.

Catalyst O (comparative catalyst)

Catalyst O is a precipitated aluminum phosphate which is obtained by precipitation from $Al(NO_3)_3/H_3PO_4$ solution with $NH_3$ at pH 6-7. The precipitate is filtered off, dried at 100° C. and then calcined at 500° C. Catalyst O contains 28.5% by weight of Al and 13.2% by weight of P.

TABLE 1

5-methylene-4,4-dimethyl-1,3-dioxolan-2-one (I) 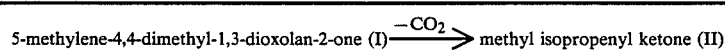 methyl isopropenyl ketone (II)

| Example | 1 | 2 | 3 | 4 | 5 | 6 | 7 | 8 | 9 | 10 | 11 | 12 | 13 | 14 | 15[(1)] | 16[(1)] |
|---|---|---|---|---|---|---|---|---|---|---|---|---|---|---|---|---|
| Catalyst | A | A | A | E | E | B | C | E | F | G | H | I | J | J | O | O |
| Temperature [°C.] | 350 | 375 | 400 | 300 | 350 | 350 | 350 | 350 | 350 | 350 | 350 | 350 | 350 | 400 | 350 | 400 |
| WHSV $h^{-1}$ | 4 | 3 | 3 | 2 | 2 | 4 | 3 | 3 | 4 | 4 | 3 | 3 | 3 | 4 | 3 | 4 |
| Conversion of I [%] | 67.9 | 84.8 | 97.4 | 80.7 | 98.0 | 80.2 | 94.4 | 85.0 | 74.3 | 76.4 | 99.6 | 98.5 | 71.7 | 98.0 | 94.0 | 98.6 |
| Selectivity [%] | | | | | | | | | | | | | | | | |
| II | 98.9 | 97.8 | 93.4 | 95.2 | 90.6 | 91.1 | 89.7 | 93.5 | 94.2 | 92.5 | 92.7 | 92.3 | 90.3 | 89.0 | 82.5 | 86.0 |

TABLE 1-continued 5-methylene-4,4-dimethyl-1,3-dioxolan-2-one (I) $\xrightarrow{-CO_2}$ methyl isopropenyl ketone (II)

| Example | 1 | 2 | 3 | 4 | 5 | 6 | 7 | 8 | 9 | 10 | 11 | 12 | 13 | 14 | 15[(1)] | 16[(1)] |
|---|---|---|---|---|---|---|---|---|---|---|---|---|---|---|---|---|
| III | — | — | — | — | 0.2 | 1.5 | 2.2 | 1.0 | 0.9 | 2.1 | — | | | 1.1 | | |

I 5-methyl-4,4-dimethyl-1,3-dioxolan-2-one dissolved in tetrahydrofuran (75% strength solution)
II Methyl isopropenyl ketone
III Dimer of II
[(1)]Comparative Example

TABLE 2

5-Methylene-4,4-dimethyl-1,3-dioxolan-2-one (I) $\xrightarrow[-CO_2]{+H_2}$ methyl isopropenyl ketone (III)

| Example | 17 | 18 | 19 | 20 |
|---|---|---|---|---|
| Catalyst | K | L | M | N |
| Temperature [°C.] | 400 | 350 | 400 | 350 |
| WHSV$^{-1}$ | 4 | 4 | 4 | 4 |
| I: H$_2$, molar | 1:6 | 1:6 | 1:6 | 1:6 |
| Conversion of I [%] | 100 | 90.1 | 100 | 73.0 |
| Selectivity [%] | | | | |
| III | 95.7 | 95.9 | 95.7 | 93.5 |

I 5-Methyl-4,4-dimethyl-1,3-dioxolan-2-one dissolved in tetrahydrofuran (75% strength solution)

We claim:

1. A process for the preparation of an unsaturated ketone of the formula (I)

$$\begin{array}{c} R^1 \\ \phantom{R^1}\diagdown \\ \phantom{R^1}\phantom{\diagdown}C=C-\overset{O}{\overset{\|}{C}}-CH_3 \\ R^2 \diagup \phantom{C=}\underset{R^3}{|} \end{array} \quad (I)$$

or a saturated ketone of the formula (II)

$$R^1-\underset{\underset{R^2}{|}}{\overset{\overset{H}{|}}{C}}-\underset{\underset{R^3}{|}}{\overset{\overset{H}{|}}{C}}-\overset{\overset{O}{\|}}{C}-CH_3 \quad (II)$$

where R$^1$, R$^2$ and R$^3$ are each hydrogen, alkyl of 1 to 12 carbon atoms or a cycloalkyl, aryl, aralkyl or alkylaryl radical, or R$^1$ and R$^3$ or R$^2$ and R$^3$, together with the carbon atoms to which they are bonded, may form a cycloalkane, wherein a 5-methylene-1,3-dioxolanone which is substituted in the 4-position and is of the formula (III)

$$\begin{array}{c} R^2 \quad R^3 \\ \phantom{R^2}\diagdown \phantom{R^3}| \\ CH-C\phantom{xx}C=CH_2 \\ R^1 \diagup \phantom{xx} O \phantom{xx} O \\ \phantom{xxxx}\diagdown \phantom{x} \diagup \\ \phantom{xxxxx}\underset{\|}{C} \\ \phantom{xxxxxx}O \end{array} \quad (III)$$

where R$^1$, R$_2$ and R$^3$ have the above meanings, (a) for the preparation of an unsaturated ketone (I), is converted in the gas phase at a temperature of from 100° to 500° C. in a fixed or fluidized catalyst bed, or in the liquid phase at a temperature of from 50° to 200° C. in the presence of a zeolite and/or of a B, Ce, Fe, Zr or Sr phosphate as catalysts and (b) for the preparation of a saturated ketone (II), is converted in the gas phase at a temperature of from 100° to 500° C. in a fixed or fluidized catalyst bed, or in the liquid phase at a temperature of from 50° to 200° C. in the presence of hydrogen over a zeolite and/or a B, Ce, Fe, Zr or Sr phosphate, which carries one or more hydrogenation components, as catalysts.

2. The process of claim 1, wherein the catalyst used is a zeolite of the pentasil type, which may furthermore carry a hydrogenation component.

3. The process of claim 1, wherein the catalyst used is an aluminum silicate zeolite of the faujasite type, which may furthermore carry a hydrogenation component.

4. The process of claim 1, wherein a hydrothermally prepared aluminum phosphate or silicon aluminum phosphate or silicon iron aluminum phosphate or iron aluminum phosphate or boron aluminum phosphate, which may furthermore carry a hydrogenation component, is used as the zeolite.

5. The process of claim 1, wherein R$^1$, R$^2$ and R$^3$ are each hydrogen, methyl or ethyl.

* * * * *